United States Patent [19]

Grossmann et al.

[11] Patent Number: 5,670,454
[45] Date of Patent: Sep. 23, 1997

[54] HERBICIDES OF THE AUXIN TYPE FOR TREATING TRANSGENIC CROP PLANTS

[75] Inventors: Klaus Grossmann, Limburgerhof; Helmut Walter, Obrigheim, both of Germany

[73] Assignee: BASF Aktiengesellschaft, Ludwigshafen, Germany

[21] Appl. No.: 572,044

[22] Filed: Dec. 14, 1995

[30] Foreign Application Priority Data

Dec. 15, 1994 [DE] Germany .................. 44 44 708.6

[51] Int. Cl.$^6$ .................. A01N 37/10; A01N 43/40; A01N 43/42
[52] U.S. Cl. .................. 504/244; 504/247; 504/254; 504/260; 504/322; 504/323; 504/324; 435/240.4
[58] Field of Search .................. 504/247, 254, 504/244, 260, 322, 323, 324; 435/240.4

[56] References Cited

U.S. PATENT DOCUMENTS

| | | | |
|---|---|---|---|
| 4,497,651 | 2/1985 | Hagen et al. | 71/94 |
| 4,715,889 | 12/1987 | Hagen et al. | 71/94 |
| 5,424,412 | 6/1995 | Brown et al. | 536/24.1 |
| 5,498,544 | 3/1996 | Gengenbach et al. | 435/320.1 |
| 5,502,271 | 3/1996 | Donn | 800/200 |

FOREIGN PATENT DOCUMENTS

| | | |
|---|---|---|
| 2091243 | 3/1992 | Canada . |
| 31 08 873 | 9/1982 | Germany . |
| 32 33 089 | 3/1984 | Germany . |
| 91 09 112 | 6/1991 | WIPO . |
| WO92/04456 | 9/1991 | WIPO . |
| 95 16 047 | 6/1995 | WIPO . |

OTHER PUBLICATIONS

Cole, D.J. "Introduction of herbicide-resistant crops". *Pesticide Outlook*. 5(3):32–36. Jun. 1994.
GROSSMANN et al., *Plant Growth Regul.* vol. 16, pp. 183–188 (1995).
GROSSMAN et al., *Plant Physiol.* vol. 142, pp. 457–466 (1993).
GRIERSON et al., *Euphytica*, vol. 79, pp. 251–263 (1994).
Herbicides, 2nd ed. vol. 1, Academic Press, pp. 255–280. L.J. Audus, ed. 1976.
Herbicide Action, Carl Fedtke, pp. 159–1976, 1982.

*Primary Examiner*—S. Mark Clardy
*Attorney, Agent, or Firm*—Keil & Weinkauf

[57] ABSTRACT

Use of herbicides of the auxin type for controlling broad-leaved weeds and grass weeds in transgenic crop plants which contain an ACC synthase antisense gene, ACC oxidase gene, ACC deaminase gene or combinations thereof is described.

6 Claims, No Drawings

HERBICIDES OF THE AUXIN TYPE FOR TREATING TRANSGENIC CROP PLANTS

The present invention relates to the use of herbicides of the auxin type for controlling broad-leaved weeds and grass weeds in transgenic crop plants which contain an ACC synthase antisense gene, ACC oxidase antisense gene, ACC deaminase gene or combinations thereof.

Herbicides of the auxin type interfere with vegetable growth promoters, the auxins, stimulating metabolic processes, leading to irregular morphology and finally to a decomposition of the tissue and dying off of the plants. The stimulation of the biosynthesis of ethylene is associated with the action of herbicides of the auxin type (Target sites for herbicide action, Plenum Press, New York, 1991, page 155, Morgan, P. W. (1976) Effect of ethylene physiology. In: Herbicides physiology, biochemistry, and ecology, page 256–280 (Audus, L. J., ed.) Academic Press, New York). The herbicides of the auxin type show excellent action against a wide spectrum of broad-leaved weeds and grass weeds. Although some crop plants such as eg. rice, rape and wheat are tolerant to, for example, quinclorac, other crop plants such as tomatoes, soybeans, cotton and corn are attacked by herbicides of the auxin type.

Herbicides of the auxin type are known and are described, for example, in DE-OS 31 08 873 and DE-OS 32 33 089.

Transgenic plants which contain an ACC synthase antisense gene are known from WO 92/04456. This gene inhibits the synthesis of 1-aminocyclopropane-1-carboxylic acid (ACC) in ethylene biosynthesis, whereby, eg. in tomatoes, ripening is suppressed, which is seen in the fact that the tomatoes remain green for months.

It is an object of the present invention to demonstrate a route which makes it possible also to use herbicides of the auxin type for controlling broad-leaved weeds and grass weeds in crop plants which normally are not tolerant to these herbicides.

We have now surprisingly found that this object is achieved by the use of herbicides of the auxin type for controlling broad-leaved weeds and grass weeds in transgenic crop plants which contain an ACC synthase antisense gene, ACC oxidase antisense gene, ACC deaminase gene or combinations thereof. Herbicides of the auxin type are known and are described in Ralph C. Kirkwood, Target sites for herbicide action, 1991 Plenum Press, New York, page 154–167 (author K. E. Pallett); Carl Fedtke, Biochemistry and physiology of herbicide action, Springer Verlag Berlin, Heidelberg 1982, pages 157–176; DE-OS 31 08 873 and DE-OS 32 33 089.

There are described, for example, herbicides of the auxin type such as phenoxyacetic acids, benzoic acids, pyridinecarboxylic acids, quinolinecarboxylic acids, acetic acids substituted by aromatics or heteroaromatics, and a few special types.

Suitable phenoxycarboxylic acids are 2,4-dichlorophenoxyacetic acid (2,4-D), 2,4-dichlorophenoxybutyric acid (2,4-DB), 2,4-dichlorophenoxypropionic acid (2,4-DP, dichlorprop), 4-chloro-2-methylphenyoxyacetic acid (MCPA), (+)-2-(4-chloro-2-methylphenoxy)propionic acid (mecoprop), 2,4,5-trichlorophenoxyacetic acid (2,4,5-T), 3,5,6-trichloro-2-pyridyloxyacetic acid (triclopyr) and their salts, esters and amides.

Suitable benzoic acids are, for example, 3-amino-2,5-dichlorobenzoic acid (chloramben), 3,6-dichloro-2-methoxybenzoic acid (dicamba), 2,3,6-trichlorobenzoic acid (2,3,6-TBA), 3,5,6-trichloro-2-methoxybenzoic acid (tricamba) and also their salts, esters and amides.

Suitable pyridinecarboxylic acids are, for example, 3,6-dichloropyridine-2-carboxylic acid (clopyralid), 4-amino-3,5,6-trichloropyridine-2-carboxylic acid (picloram) and also their salts, esters and amides.

Suitable quinolinecarboxylic acids are, for example, 3,7-dichloroquinoline-8-carboxylic acid (quinclorac), 7-chloro-3-methylquinoline-8-carboxylic acid (quinmerac) and also their salts, esters and amides.

Suitable acetic acids substituted by aromatics or heteroaromatics are, for example, 4-chloro-2,3-dihydro-2-oxo-1,3-benzothiazol-3-ylacetic acid (benazolin), 2,3,6-trichlorophenylacetic acid (fenac), indol-3-ylacetic acid (IAA), 1-naphthylacetic acid (NAA) and also their salts, esters and amides.

A few special types of herbicides of the auxin type are, for example, orthonil and 4-amino-3,5-dichloro-6-fluoro-2-pyridyl-oxyacetic acid (fluoroxypyr).

Quinclorac and quinmerac are preferably used.

Transgenic crop plants which contain a 1-aminocyclopropane-1-carboxylic acid (ACC) synthase antisense gene are described in WO 92/04456, including their preparation by genetic engineering and the isolation of the underlying DNA. This ACC synthase antisense gene is responsible for the fact that the synthesis of the direct ethylene precursor 1-aminocyclopropane-1-carboxylic acid (ACC) is prevented in the biosynthesis of the phytohormone ethylene, whereby the ripening process of the crop plants is stopped, which is seen, eg. in the case of tomatoes, in the absence of reddening.

According to J. E. Gray, Plant, Cell and Environment (1994) 17, 557 to 571, in addition to ACC synthase ACC oxidase and ACC deaminase also intervene in plant ethylene biosynthesis. ACC synthase and also ACC oxidase are encoded in the plant by gene families. The expression of these genes is induced as a function of the development of the plants or by exertion of influence by environmental factors. ACC deaminase genes were until now isolated from soil bacteria and incorporated into transgenic plants. While the ACC oxidase antisense genes inhibit the conversion of ACC to ethylene, ACC deaminase genes lead, in the orientation sense introduced into the plant, to the decomposition of the ACC synthesized. In all cases, the formation of the phytohormone ethylene is reduced by this or almost completely inhibited.

It has now surprisingly been found that the transgenic crop plants described in WO 92/04456, which contain an ACC synthase antisanse gene, are tolerant to the abovementioned herbicides of the auxin type.

The herbicides of the auxin type or the herbicidal compositions containing them and their environmentally tolerable salts, eg. of alkali metals, alkaline earth metals or ammonia and amines or the herbicidal compositions thus containing them, can very effectively control broad-leaved weeds and grass weeds in the transgenic crops such as tomatoes, corn, soybeans and cotton, without damaging the transgenic crop plants, an effect which especially occurs even at low application rates. Taking into account the versatility of the application methods, the herbicides of the auxin type or compositions containing them can additionally be employed for the elimination of undesired plants in a further number of crop plants. Examples of suitable crops are the following:

*Allium cepa, Ananas comosus, Arachis hypogaea, Asparagus officinalis, Beta vulgaris spp. altissima, Beta vulgaris spp. rapa, Brassica napus var. napus, Brassica*

*napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spp., Manihot esculenta, Medicago sativa, Musa spp., Nicotiana tabacum (N.rustica), Olea europaea, Oryza sativa, Phaseolus lunatus, Phaseolus vulgaris, Picea abies, Pinus spp., Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

The application of the herbicidal compositions or of the herbicides of the auxin type can be carried out pre-emergence or post-emergence. If the active compounds are less tolerable for certain crop plants, application techniques can be used in which the herbicidal compositions are sprayed with the aid of the spray equipment such that if possible the leaves of the sensitive crop plants are not affected, while the active compounds reach the leaves of undesired plants growing under them or the uncovered soil surface (post-directed, lay-by).

The herbicides of the auxin type or the herbicidal compositions containing them can be applied by spraying, atomizing, dusting, broadcasting or watering, for example in the form of directly sprayable solutions, powders, suspensions, even high-percentage aqueous, oily or other suspensions or dispersions, emulsions, oil dispersions, pastes, dusting compositions, broadcasting compositions or granules. The application forms depend on the intended uses; in each case if possible they should ensure the finest dispersion of the active compounds according to the invention.

Suitable inert additives are, inter alia, mineral oil fractions of medium to high boiling point, such as kerosene or diesel oil, and also coal tar oils and oils of vegetable or animal origin, aliphatic, cyclic and aromatic hydrocarbons, eg. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, suspensions, pastes, wettable powders or water-dispersible granules by addition of water. To prepare emulsions, pastes or oil dispersions, the substrates as such or dissolved in an oil or solvent can be homogenized in water by means of wetting agents, adhesives, dispersants or emulsifiers. However, concentrates consisting of active substance, wetting agents, adhesives, dispersants or emulsifiers and possibly concentrates consisting of solvent or oil can also be prepared, which are suitable for dilution with water.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols and of fatty alcohol glycol ethers, condensation products of sulfonated naphthalene and its derivatives with formaldehyde, condensation products of naphthalene or of naphthalenesulfonic acids with phenol and formaldehyde, polyoxyethylene octylphenol ethers, ethoxylated isooctyl-, octyl- or nonylphenol, alkylphenyl or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powder, broadcasting and dusting compositions can be prepared by mixing or joint grinding of the active substances with a solid carrier.

Granules, eg. coated, impregnated and homogeneous granules can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products such as cereal flour, tree bark meal, wood meal and nutshell meal, cellulose powder or other solid carriers.

The formulations in general contain from 0.01 to 95% by weight, preferably from 0.5 to 90% by weight, of active compound. The active compounds are employed here in a purity of from 90% to 100%, preferably from 95% to 100% (according to NMR spectrum).

The herbicides of the auxin type can be formulated, for example, as follows:

I. 20 parts by weight of 3,7-dichloroquinoline-8-carboxylic acid (quinchlorac) are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

II. 20 parts by weight of 7-chloro-3-methylquinoline-8-carboxylic acid (quinmerac) are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

III. 20 parts by weight of 3,7-dichloroquinoline-8-carboxylic acid are dissolved in a mixture which consists of 25 parts by weight of cyclohexanone, 65 parts by weight of a mineral oil fraction of boiling point from 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IV. 20 parts by weight of 3,7-dichloroquinoline-8-carboxylic acid are well mixed with 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel and ground in a hammer mill. By finely dispersing the mixture in 20,000 parts by weight of water, a spray mixture is obtained which contains 0.1% by weight of the active compound.

V. 3 parts by weight of 3,7-dichloroquinoline-8-carboxylic acid are mixed with 97 parts by weight of finely divided kaolin. In this manner, a dusting composition is obtained which contains 3% by weight of the active compound.

VI. 20 parts by weight of 3,7-dichloroquinoline-8-carboxylic acid are intimately mixed with 2 parts by weight of calcium salt of dodecylbenzenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

To broaden the spectrum of action and to achieve synergistic effects, the herbicides of the auxin type can be mixed and applied jointly with numerous representatives of other herbicidal or growth-regulating active compound groups. For example, suitable mixture components are diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry eg. a carboxyl or carbimino group in the 2-position, quinolinecarboxylic acid derivatives, imidazolinones, sulfonamides, sulfonylureas, aryloxy- and heteroaryloxyphenoxypropionic acids and their salts, esters and amides and others.

It may additionally be of use to apply the herbicides of the auxin type on their own or jointly in combination with other herbicides also additionally mixed with further crop protection agents, for example with agents for controlling pests or phytopathogenic fungi or bacteria. Also of interest is the miscibility with inorganic salt solutions which are employed for eliminating nutritional and trace element deficiencies. Non-phytotoxic oils and oil concentrates can also be added.

Depending on the target of control, time of year, target plants and growth stage, the application rates of active compound are from 0.001 to 3.0, preferably from 0.01 to 1.0 kg/ha of active substance (a.s.)

EXAMPLE

Wild-type tomato plants (variety VF-36, non-transformed) and homozygotic antisense plants of the transformant A 11.1 (A 11.1 -10-17; fifth generation) which contained the constitutively expressed antisense construct pPO 35 to ACC synthase gene LE-ACC 2 (Oeller PW, Min-Wong L, Taylor LP, Pike DA and Theologis A (1991) Reversible inhibition of tomato fruit senescence by antisense RNA, Science 254; 437 to 439) were cultivated at 24/20° C. in soil in 200 ml pots (one plant per pot) with a light/dark alternation of 15/9 hours. The seed was made available by the Plant Gene Expression Center, Albany, Calif., U.S.A. In the second leaf stage, 3 weeks after sowing, the plants (5 duplicates) were treated via the soil with a single application of 20 ml per plant of an aqueous solution of 0.1, 0.5 and 5 mg of quinclorac. In this test, the active compound was dissolved in 0.4 ml of a mixture of 1 part by volume of DMSO and 10 parts by volume of methanol and diluted with water.

Only the solvent was applied to the untreated control plants. The growth parameters were determined 12 days after treatment. Table I shows the effect of quinclorac on fresh shoot mass and plant height of the wild-type plant (VF-36). Table II shows the effect of quinclorac on fresh shoot mass and plant height of the antisense plant (A 11.1). The data are in each case mean values from 5 tomato plants each (± standard error). Values with identical letters are not significantly different (p=0.1, Duncan's multiple range test).

TABLE I

| Wild-type tomato (VF-36) | | |
| --- | --- | --- |
| Quinclorac [mg/plant] | Fresh shoot mass [g] | Plant height [cm] |
| 0 | 5.8 ± 0.5 a | 16.1 ± 1.0 a |
| 0.1 | 3.9 ± 0.7 b | 12.1 ± 0.8 b |
| 0.5 | 2.6 ± 0.4 c | 11.6 ± 0.6 b |
| 5.0 | 0.9 ± 0.2 d | 8.5 ± 0.9 c |

TABLE II

| Antisense tomato (A 11.1) | | |
| --- | --- | --- |
| Quinclorac [mg/plant] | Fresh shoot mass [g] | Plant height [cm] |
| 0 | 5.8 ± 0.5 a | 15.4 ± 0.6 a |
| 0.1 | 6.7 ± 0.9 a | 16.1 ± 1.3 a |
| 0.5 | 5.1 ± 0.8 a | 14.7 ± 0.8 a |
| 5.0 | 0.8 ± 0.2 b | 8.2 ± 0.4 b |

The values in Table II clearly show the tolerance of the antisense tomato to quinclorac up to an amount of 0.5 mg/plant. The tomato plant is damaged only at 5 mg, whereas the damage to the wild-type tomato plant begins even at 0.1 mg/plant of quinclorac.

We claim:

1. A method for controlling broad-leaved weeds and grass weeds in transgenic crop plants which contain an ACC synthase antisense gene, ACC oxidase antisense gene, ACC deaminase gene or combinations thereof by treating the broad-leaved weeds, grass weeds and transgenic crop plants with herbicides of the auxin type.

2. The method as claimed in claim 1, the herbicides of the auxin type being selected from the group consisting of phenoxycarboxylic acids, pyridine- carboxylic acids, quinolinecarboxylic acids, acetic acids substituted by aromatics or heteroaromatics, and their salts, esters and amides.

3. The method as claimed in claim 1, the herbicides of the auxin type being selected from the group 2,4-D, 2,4-DB, MCPA, mecoprop, dichlorprop, 2,4,5-T, triclopyr, chloramben, dicamba, 2,3,6-TBA, tricamba, clopyralid, picloram, quinmerac, quinclorac, benazolin, fenac, IAA, NAA, orthonil and fluroxypyr.

4. The method as claimed in claim 3, quinmerac or quinclorac being employed as herbicides of the auxin type.

5. The method as claimed in claim 1, the transgenic crop plants being selected from the group consisting of tomatoes, cotton, soybeans and corn.

6. The method as claimed in claim 1, transgenic crop plants being selected which contain an ACC synthase antisense gene.

* * * * *